United States Patent
Rushbrooke et al.

(10) Patent No.: US 6,646,272 B2
(45) Date of Patent: Nov. 11, 2003

(54) FIBER OPTIC COUPLING DEVICE FOR DETECTING LUMINESCENT SAMPLES

(75) Inventors: John Gordon Rushbrooke, Cambridge (GB); Claire Elizabeth Hooper, Cambridge (GB); William Wray Neale, Great Wilbraham (GB)

(73) Assignee: Packard Instrument Company, Inc., Meriden, CT (US)

( * ) Notice: Subject to any disclaimer, the term of this patent is extended or adjusted under 35 U.S.C. 154(b) by 0 days.

(21) Appl. No.: 10/008,008

(22) Filed: Nov. 8, 2001

(65) Prior Publication Data

US 2002/0070350 A1 Jun. 13, 2002

Related U.S. Application Data

(63) Continuation of application No. 09/214,915, filed as application No. PCT/GB97/01825 on Jul. 4, 1997, now Pat. No. 6,392,241.

(30) Foreign Application Priority Data

Jul. 10, 1996 (GB) ............................................... 9614528
Oct. 1, 1996 (GB) ............................................... 9620437
Dec. 3, 1996 (GB) ............................................... 9625132

(51) Int. Cl.$^7$ ............................................... G01N 21/64
(52) U.S. Cl. ............................... 250/461.1; 250/461.2; 385/120
(58) Field of Search ........................... 250/461.1, 461.2, 250/359.1, 360.1, 370.8; 385/120

(56) References Cited

U.S. PATENT DOCUMENTS

| | | | | |
|---|---|---|---|---|
| 4,922,092 A | * | 5/1990 | Rushbrooke et al. | 250/214 VT |
| 4,957,114 A | * | 9/1990 | Zeng et al. | 250/214 VT |
| 5,042,494 A | * | 8/1991 | Alfano | 600/477 |
| 5,122,657 A | * | 6/1992 | De Bie et al. | 250/227.2 |
| 5,699,795 A | * | 12/1997 | Richards-Kortum et al. | 600/478 |
| 5,830,134 A | * | 11/1998 | Caputo et al. | 422/82.09 |
| 5,930,433 A | * | 7/1999 | Williamson et al. | 356/444 |
| 5,998,802 A | * | 12/1999 | Struye et al. | 250/584 |

* cited by examiner

*Primary Examiner*—Albert Gagliardi
(74) *Attorney, Agent, or Firm*—Barnes & Thornburg (57) ABSTRACT

A fiber optic coupling plate (24) has a sample viewing face for receiving light from a sample (12), an output window (18) for conveying sample originating (emitted) light to an imaging detector and an additional window through which excitation radiation can be projected. A primary light is provided through the plate made up of optical fibers which will convey light entering the viewing face, directly and with minimal loss, to the output window, and a secondary light path separate from the primary light path, by which excitation radiation entering the additional window is conveyed to the viewing face for irradiating the sample.

5 Claims, 11 Drawing Sheets

Fig. 3   UV TRANSMITTING GLASS

FIBER OPTIC COUPLING DEVICE FOR DETECTING LUMINESCENT SAMPLES

RELATED APPLICATION

This application is a continuation of U.S. patent application Ser. No. 09/214,915 filed Jul. 26, 1999, now U.S. Pat. No. 6,392,241, which is the national filing of international application no. PCT/GB97/01825, filed Jul. 4, 1997.

FIELD OF INVENTION

This invention concerns methods and apparatus for imaging, particularly the imaging of fluorescing samples of the type in which the sample is first illuminated with an excitation radiation such as ultra-violet light and is subsequently interrogated for any resulting emission light due to fluorescence from within the sample.

Typically a sample will comprise an array of a large number of sites each containing a small quantity of material or mixture of materials under investigation, and one convenient array comprises a plate containing a large number of wells arranged in a rectangular matrix each of which comprises a site; or a membrane, or a dish, over the surface of which exist a large number of reaction sites which are to be investigated.

For the purpose of investigation an image of each of the sites (preferably all at the same time) is formed at the input to a detector which converts light into electrical signals. The detector may comprise a CCD camera which may be cryogenically cooled or may comprise a CCD camera preceded by or including an image intensifying device.

BACKGROUND OF THE INVENTION

It is known from U.S. Pat. No. 4,922,092 to utilize a fibre optic device to couple the light emitted from such an array of sites to such imaging devices.

It is an object of the present invention to provide a device by which an array of such sites can be coupled to a source of excitation radiation (such as a source of UV light), as well as to the input of an imaging device, so that after exposure to excitation radiation, the sites can be inspected for any fluorescence arising therefrom.

The invention will be of particular benefit where the sites are small and closely packed together as in the case of high density multi-well plates.

SUMMARY OF THE INVENTION

According to one aspect of the present invention there is provided a fibre optic coupling plate having a sample viewing face for receiving light from a sample, an output window for conveying sample originating (emitted) light to an imaging detector and an additional window through which excitation radiation can be projected, wherein there are provided a primary light path through the plate made up of optical fibres which will convey light entering the viewing face, directly and with minimal loss, to the output window, and a secondary light path separate from the primary light path, by which excitation radiation entering the additional window is conveyed to the viewing face for irradiating the sample.

The coupling plate preferably includes radiation reflecting or absorbing means to restrict the exit of excitation radiation therefrom except as required to irradiate the sample.

To this end, and where the material forming the coupling plate is not opaque to the excitation radiation, the optical fibres forming the primary path may be coated or sleeved with a material resistant to the transmission of the excitation radiation, and those areas of the output window not occupied by the optical fibre ends are rendered impervious to excitation radiation to prevent the latter from exiting in the direction of the detector.

The primary light path fibres are preferably formed from a material which readily transmits light emitted from the sample but only poorly transmits excitation radiation wavelengths.

The secondary path may comprise a second set of optical fibres which are bundled with the first set of fibres forming the primary path, and the fibres of both sets terminating in and comprising at least part of the sample viewing face.

The ends of the fibres from the two sets may be interspersed in a random manner across the face of the sample viewing window or may be arranged in a particular pattern so that the fibres of the first set bear a fixed relationship both in position and number relative to the fibres of the second set.

Where the second path is comprised of fibres, they are preferably formed from a material which readily transmits excitation radiation wavelengths.

In a preferred arrangement, the secondary path comprises selected optical material which is capable of transmitting the excitation radiation and which surrounds, but is optically screened, from the optical fibres which convey the image light to the output window.

The selected material is preferably in the form of a sleeve around each of the fibres of the first set, although in some circumstances it may be in the form of a block of material through which all the fibres in the first set extend.

In a particularly preferred arrangement, the coupling plate is formed from the said selected optical material and the fibres conveying the light from the sample to the detector are coated or sleeved with a material which is impervious at least to the excitation radiation wavelengths.

The optical screening is most simply provided by a coating the fibres making up the said first set. In known manner the coating material is selected so that it not only serves to reflect any internal radiation (so as to improve the efficiency of the fibres), but is also selected so as to be reflective at the wavelengths of the excitation radiation so that it not only prevents the latter from entering the fibres but also renders available and useful reflected excitation radiation for subsequent reflection and possible emission out of the coupling plate towards the sample as required.

By coating the fibres with a suitable material light within the fibres is completely prevented from escaping into the plate material surrounding them.

According to a particularly preferred aspect of the invention, each of the optical fibres in the first set is replaced by a bundle of parallel very small diameter fibres, each of which is coated as aforesaid to prevent the ingress of excitation radiation and the exit of light from within the fibre.

Preferably the small diameter fibres in each bundle are also separated one from the other by the said selected optical material which also surrounds and separates one bundle of fibres from adjacent bundles of fibres.

In one embodiment the plate includes a large number of separate fibres, (or fibre bundles) as aforesaid, distributed substantially uniformly across at least the input face area of the plate, each fibre or bundle of fibres extending from the input face to another face thereof, which serves as the output window.

If the density (ie the number per unit area) of the fibres (or bundles), across the face, is sufficiently high, it may not be essential for the fibres or bundles to be arranged in any particular pattern or have any particular spacing as between one and the next so long as each is a discrete isolated light path.

According to a further aspect of the invention, the input face area may be larger than the input window area so that the density of the fibres or bundles in the latter is greater than is the density of the fibres or bundles in the former.

According to a further aspect of the invention, where a coupling plate as aforesaid is to be used with a sample having a regular array of reaction sites, (or wells) then the fibres (or bundles of fibres) are preferably arranged (at least over the input face of the plate) in the same pattern and with the same interstitial spacing as are the sites in the sample, so that registration is possible between sites and fibres (or fibre bundles), one fibre (or fibre bundle) registering with each site.

Where the coupling plate is formed from selected optical material and the latter is used as the medium for conveying the excitation radiation, it is simply necessary for part of the well or site to communicate with a small region of the material forming the coupling plate to enable excitation radiation to exit thereinto.

Where each site is "seen" by one or a few large area fibres, the area of the end of each such fibre (or group of fibres) in the input face must be somewhat less than the area of the site or well with which it cooperates, so that at least part of each site registers with an area of the input face of the coupling plate not occupied by optical fibre(s) leading to the output window, so that excitation radiation can exit therethrough into the site or well.

Where for example the wells are circular and large diameter circular section fibres are centered relative to the wells or sites, the diameter of the fibre being less than that of the well, there will be an annulus of selected optical (plate) material around the fibre through which excitation radiation can pass to the sample.

However, the more preferred arrangement comprises a fibre bundle associated with each site, in which the individual fibres are spaced apart by the said selected optical material from which the plate is also formed, and the area of the bundle is commensurate with the area of the site or well. Excitation radiation is conveyed to the site or well through the material separating the individual fibres in each bundle. This has the benefit that the excitation radiation will tend to be more or less uniformly distributed over the area of the bundle and therefore the site or well so that excitation radiation is very closely coupled to all regions in the well or site which might react thereto. Where some assays are concerned, this is of considerable importance.

In a coupling plate as aforesaid, it has been found that excitation radiation can be conveyed to the sites or wells, coupled to the input face thereof, by simply directing excitation radiation edgewise into the plate when and as required. Where the sites and fibres (or fibre bundles) are arranged in the same pattern and with the same spacing, the transfer of excitation radiation into the sites is best accomplished when the fibres (or bundles) are centered relative to the sites.

In one arrangement the number of fibres (or fibre bundles) is the same as the number of sites in the sample. However with the tendency towards ever increasing numbers of sites per sample, an alternative arrangement is one in which the number of fibres (or fibre bundles) is a fraction of the number of sites in the sample and all of the latter can be inspected, albeit in a sequence of steps, by moving the sample relative to the coupling plate input face (or vice versa) until all of the sites have been brought into registry with the fibres (bundles of fibres) at one time or another in the said sequence of steps.

Where the excitation radiation is in the ultra-violet the said select optical material may be silica glass.

Where the fibres extend into the input window surface, the area of the window surrounding each fibre (whether large individual ones or small diameter fibres making up bundles) may be rendered opaque to ultra-violet radiation by acid etching the silica glass, coating the whole surface of the output window with a titanium dioxide or epoxy and then grinding the coating material down to expose the ends of the fibres while leaving the coating material in the troughs created by the etching process in the surface of the glass surrounding the fibres. In this way only the fibre ends extend through the coating material and by a choice of suitable coating material such as suggested; ultra-violet radiation within the coupling plate can be prevented from exiting around the fibre ends towards the detector.

As indicated above, the excitation radiation may be projected edgewise into the coupling plate and this edgewise projection may take one of a number of different forms.

In one arrangement a single source of excitation radiation is directed through a single window in the edge of the plate, and the edge and output face surface of the plate are all coated (eg with titanium dioxide/epoxy) so that the only exit path for excitation radiation is towards the sample, through the optical material from which the coupling plate is formed which surrounds the fibre in the input face.

Modifications of this arrangement involve the use of two, three or more such radiation sources arranged symmetrically around the coupling plate, each having its own input window through which radiation therefrom can be projected into the coupling plate.

In a preferred arrangement, the whole of the edge of the plate is left as an input window for excitation radiation, and the coupling plate is embraced and completely surrounded by excitation radiation from one or more sources arranged thereon around. Reflecting means may be provided external to the plate more evenly to distribute the radiation towards the edge of the coupling plate.

Filters or shutters may be provided so as to prevent the ingress of excitation radiation except when required. Absorption filters may be provided for absorbing any excitation radiation which may leak via the fibres at the output window. This latter feature may be important where the detector is sensitive to the excitation radiation wavelengths as well as the fluorescence wavelengths (as is normally the case) since any leakage of excitation radiation into the input ends of the fibres either, directly, or alter reflection from the sample, could swamp or even destroy the detector the sensitivity certainly temporarily, if not permanently.

By coupling the plate directly to the sites or wells and to the input window of the detector means (whether a CCD camera or an image intensified camera or an image intensifier), cross-talk (caused by a region of the detector receiving light from the fluorescence occurring in two more sites) has been found to be virtually eliminated. This allows adjacent sites to be imaged simultaneously which speeds up the inspection process.

This advantage is also important since it may be desirable to be able to irradiate and then check for fluorescence very quickly and without previous multiple exposures to excitation radiation. The invention allows all of this to occur since all of the sites which are irradiated are immediately available for detection, and in general sites which are not available for detection are not irradiated.

The invention also lies in a method of checking for fluorescence in a sample, comprising the steps of irradiating the sample with excitation radiation, removing or ceasing the excitation radiation, and conveying any fluorescent light arising from the sample via fibre optic means to the input of a detector, wherein the excitation radiation is projected into a coupling plate through which the optical fibres extend, and the plate includes an optical path by which the excitation radiation can exit to the sample.

The invention also lies in apparatus for imaging fluorescence light arising from reaction sites in a pre-excited sample, comprising a sample holder, a coupling plate adjacent the holder having fibre optic means extending from the face thereof adjacent the sample holder to an input window of a detector such as an image intensifying CCD camera, a source of excitation radiation, housing means containing the source and the coupling plate, an optical path through the coupling plate for conveying excitation radiation to at least one area of the face of the plate adjacent the sample holder, means preventing excitation radiation from leaving the coupling plate at least in the direction of input window of the detector, means for controlling either the excitation radiation source or shutter means, so as to enable excitation radiation to be projected into the coupling plate only when required, signal processing means receptive of electrical signals from the detector means for at least storing and/or displaying the electrical signals as visually distinguishable regions in a visual display corresponding to part of or the whole of the input window of the detector. To this end the signal processing means may comprise windowing and/or scaling means to enable signals from only part of the area of the input window to be displayed as a full screen display in the visual display device.

The latter may comprise a television camera or LCD panel and preferably is such as to enable different colors to be displayed.

Preferably the signal processing circuit means attributes different colors to different intensities of light incident on the detector.

Where wavelength discrimination is also required, filter means may be provided to enable the detector to be responsive first of all to one wavelength, and then another.

Each image may be stored and then displayed either in sequence or simultaneously in registration. The visually distinguishable regions therein corresponding to the different light emissions may be displayed in different colors for example according to wavelength and/or intensity of the light received by the detector.

In some circumstances, optimal coupling between the sample and the plate and/or between the plate and detector has been found to occur when a very small gap is provided between the sample and the input face of the coupling plate and/or between the output window and the input window of the detector. The size of any such gap must be such as to not permit an unacceptable increase in cross-talk to occur. However a gap between the sample and the input face of the coupling plate, assists in permitting sliding movement of one device relative to the other, where as will normally be the case, the area of the input face of the coupling plate is significantly smaller than the overall area of the sample, so that it is necessary to move the sample relative to the coupling plate (or vice versa) to allow all of the sites on the sample to be irradiated and inspected.

In apparatus as aforesaid, drive means may be provided for accurately indexing the sample holder relative to the coupling plate (or vice versa).

The drive means is preferably computer controlled and the latter may also be programmed to control the production of the excitation radiation (or the operation of a shutter or other device for exposing the coupling plate to the excitation radiation), as required, and for whatever duration is required Both the indexing and the exposure and/or the exposure duration are preferably separately and independently programmable.

Although the invention is of particular application to multi-well sample plates in which each of the wells comprises a reaction site which is to be exposed and investigated, and these are essentially viewed from below through the coupling plate, the invention is not limited to such an arrangement, and where the sites are located on a medium or support surface through which light is only inefficiently or inadequately transmitted, the coupling plate may be inverted so that it is in contact with, or very close to, the surface on which the sites are located, so that excitation radiation is now directed in a downward sense through the coupling plate and it is upwardly directed light caused by fluorescence instigated by the irradiation which is detected.

Where universal apparatus is to be provided in which a sample can be inserted for viewing either above or below, two coupling plates may be provided with appropriate light paths from a common excitation radiation source, or separate excitation radiation sources may be provided, one for each coupling plate. The one plate may be above, and the other below, a sample holder which is adapted to receive multi-well plates or petri dishes or the like and which can be viewed from above or below. The fibre optic bundle in the upper coupling plate may be extended beyond the plate in the form of an umbilical which is curved through 180° to extend in a downward sense to an output window remote from the upper coupling plate. The two output windows, the one relating to the lower coupling plate and the other corresponding to the exit end of the fibre optic bundle from the other coupling plate, may be arranged side by side in the same plane and a single detector may be movable by drive means from a position where it registers with the output window of the underside plate to a position where it registers with the exit end of the fibre optic bundle from the upper plate.

Alternatively prism means, mirror means or lens means may be used to enable light from both fibre optic bundles to be imaged onto the input window of a single detector, although because of aperture problems associated with lenses this latter option may not normally be available in low light conditions.

Alternatively two separate detectors are provided one for the upper and one for the lower coupling plates.

Drive means may also be provided within such apparatus for moving the coupling plate (5) towards and away from the sample holder, and where two such coupling plates are provided, separate drive means is provided for each, so that having inserted a sample and indicated to the apparatus whether it is to be inspected from above or below, the appropriate drive means is engaged for moving the appropriate coupling plate towards the sample. Sensing means may be provided for determining when the coupling plate occupies the desired position for irradiating and inspecting the sample.

In the event that radiation and inspection is required from above and below, both coupling plates may be moved into position to permit irradiation and detection of fluorescence by one and/or then the other or both simultaneously.

It will be noted that in the case of an apparatus having above and below coupling plates, the sample may be irradiated using the excitation radiation source associated with one coupling plate and any resulting fluorescence may be detected using the detector associated with the other coupling plate.

According to a further feature of the present invention the optical fibres forming the primary light path in the coupling plate are arranged in groups, and each group is arranged to receive emission radiation from a single sample site, to transfer the emission radiation from that site to a discrete region of the output window viewed by the camera.

Conveniently the groups form fibre optic bundles.

Preferably the external surface of the fibres making up each bundle, or at least the outside surface of the bundle, is formed with an opaque coating, typically a radiation reflecting surface. Conveniently titanium dioxide paint may be used.

Typically the area of cross-section of the input end of each bundle is commensurate with but a little smaller than the cross-section area of the sample site from which radiation may be emitted into the bundle.

Since it is necessary for excitation radiation to enter the sample site so as to initiate fluorescence and thereby generate emission radiation, the input end of each bundle is preferably spaced from the underside of the reaction site by a small distance and an annular window is provided through which excitation radiation can pass into the base of the reaction site, around the end of the bundle.

Preferably an annular shield is provided around the end of the bundle so as to prevent direct ingress of excitation radiation into the input end of the bundle, and to generally direct excitation radiation towards the outer annular region of the reaction site, through which region the excitation radiation passes.

In a preferred arrangement, a plurality of reaction sites are arranged in the form of wells in a so-called multi-well plate, the wells and the fibre optic bundles are generally circular in cross-section, the well sites all have the same diameter, the fibre optic bundles are all of another slightly smaller diameter, and the circular cross-section fibre optic bundles are centrally aligned, one below each well site. For simplicity the base of each well is transparent to both emission and excitation radiation and in order to reduce cross-talk between adjacent well sites an apertured opaque plate may be located immediately below the wells, the apertures in the plate being circular and spaced so as to align with the wells. By making the diameter of each aperture just a little larger than the internal diameter of the corresponding well with which it is aligned, and by making the outside diameter of the fibre optic bundle viewing the underside of the well slightly smaller in diameter than the internal diameter of the well, a small annular region will exist through which excitation light can enter the well, around the outside of the fibre optic bundle and within the opening in the opaque plate.

Instead of forming openings in an opaque plate, the latter may be formed from material which is transparent to both excitation and emitted wavelength, and those regions which are required to be opaque are coated or impregnated with an appropriate non transmittive material, typically a reflective material, so as to inhibit the passage of either excitation or emitted radiation except through the untreated window regions left in the plate.

The windows may be formed from the same material as is the base of the wells. A clear polystyrene material may be used.

Where the underside of the well window is spaced from the end of the fibre optic bundle the gap between it and the end of the fibre optic bundle is preferably filled with a transparent material having a similar refractive index to that of both the well base and, if provided, the intermediate window.

Where clear polystyrene is used for the well base and the window material, a clear polystyrene plug may be located between the end of the fibre optic bundle and the underside of the base or the window in the plate.

Where an opaque and preferably reflecting annular shield is provided around the end of the fibre optic bundle to reduce the possibility of excitation radiation directly entering the fibres in the bundle, the annular shield preferably also extends around the plug of transparent material between the end of the fibre optic bundle and the underside of the well.

In a particularly preferred arrangement, the end of the fibre optic bundle may be surrounded by an annular sleeve of excitation wavelength transmittive material, the inner surface of which is formed with an opaque and possibly reflective coating, to prevent the passage of excitation or emitted radiation therethrough, and the fibre optic bundle terminates part way through the sleeve and a transparent plug may be fitted into the remaining space within the annular sleeve.

The annular sleeve may serve as a diffuser and be constructed accordingly.

Typically the external diameter of the annular sleeve is the same as the diameter of the window in the opaque plate.

Where the opaque plate is apertured, the annular sleeve may be fitted and secured into the window so that one end of the annular sleeve, together with the central plug above the fibre optic bundle end, is flush with the surface of the apertured plate which cooperates with the underside of the well(s).

The apertured plate may be bonded to the underside of the wells or a small gap may exist as would be the case where it is necessary to be able to replace one array of wells with another.

Typically the wells are formed in a single plate called a well-plate.

According to a preferred feature, the transparent plug fitted within the annular sleeve surrounding the end of the fibre optic bundle may be formed from filter material so that radiation of one wavelength is favored relative to radiation of another.

By selecting the characteristics of the filter material forming the plug, the latter may serve to restrict the entry of excitation wavelengths into the fibre optic bundle and/or favor emitted radiation of one wavelength as opposed to emitted radiation of other wavelengths.

In one embodiment of the present invention, the output end of the fibre optic plate is coupled to a camera input window via a filter. The purpose of the filter is to restrict wavelengths entering the camera to those of expected, or wanted, emissions so as to ideally remove from the camera input any radiation at unwanted wavelengths such as stray excitation radiation transmitted via the fibre optic plate, or the like.

In an example involving 96 fibre optic bundles, the 96 outputs of the bundles may be arranged in any convenient configuration or aspect ratio depending on the output of the camera to which the image is to be applied. Where the latter is generally circular, the 96 rods may be arranged in a generally circular or hexagonal array so as to substantially fill the entrance window of the camera, and if the latter is 40 mm diameter and the rods fill an area of 32×42 mm, there should be adequate spacing between rod centers (approximately 2.5 mm) to ensure minimal cross-talk between bundles. Where an emission filter is inserted between the plate and the camera input, this should be as thin as possible, and may need to be less than 0.5 mm to ensure acceptable levels of cross-talk.

BRIEF DESCRIPTION OF THE DRAWINGS

The invention will now be described with reference to particular examples, and with reference to the accompanying drawings, hereinafter referred to, in which.

DETAILED DESCRIPTION OF THE DRAWINGS

Figure 1:
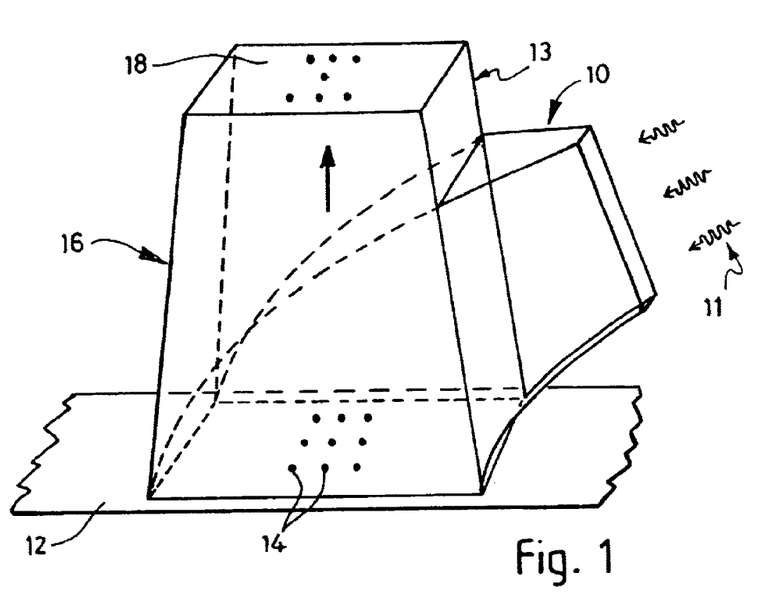
FIG. 1 illustrates one adaptor plate embodying the invention.
Figure 2:
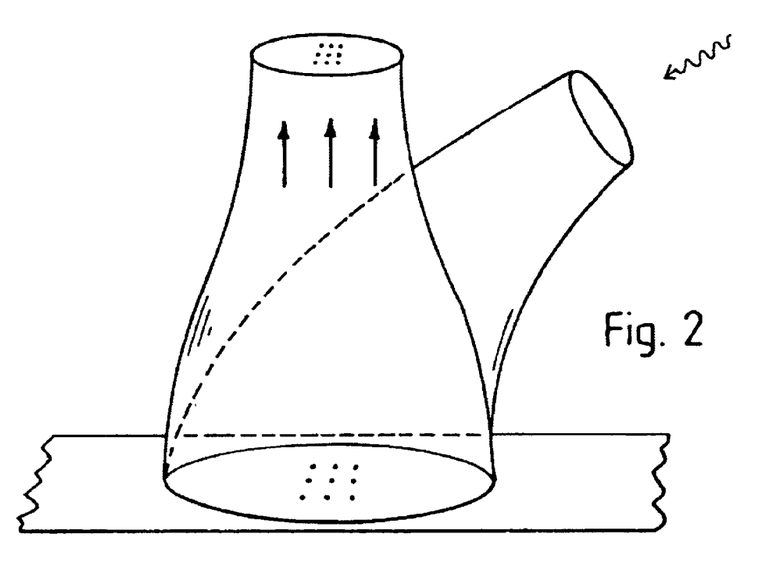
FIG. 2 is a similar view of another adaptor plate embodying the invention.

One embodiment of the invention is shown in FIG. 1. This is based on the use of fibre optic combiners/duplicators (splitters) as illustrated in FIG. 17 of the Galileo Technical Memorandum 100, entitled "Fibre Optics—Theory and Applications". Such fibre optic components are manufactured using a technique of interleaving layers of fibre bundles, which are made as typically 50 um thick ribbons, arranged in strips. As indicated in the Galileo article, individual ribbons can be diverted into two directions at one end and combined to make a fused bundle at the other. If required, the entire assembly can be constituted as a fused or integrated fibre optic device.

FIG. 1 shows how such an integrated device can be used for fluorescence contact imaging. Here one ribbon (i.e. fiber) in every five fibers is utilized for transmitting excitation illumination to a sample 12 containing wells 14, and the remaining four fibres in every five convey light from the wells 14 to an input faceplate of a detector (not shown) such as a COD camera. An example of such a detector input faceplate is shown at 52 in FIG. 7.

The fibers which are to transmit excitation illumination 11 to the wells 14 exit as bundle 10 in FIG. 1, and the remaining fibres which receive light from the wells constitute the bundle 13 which has an output face 18 in which the fibres terminate. It is this face 18 which is available to couple to an input faceplate of the detector. The latter may comprise a CCD camera which may include image-intensifying means or pay be a cryogenically cooled device.

Figure 3:
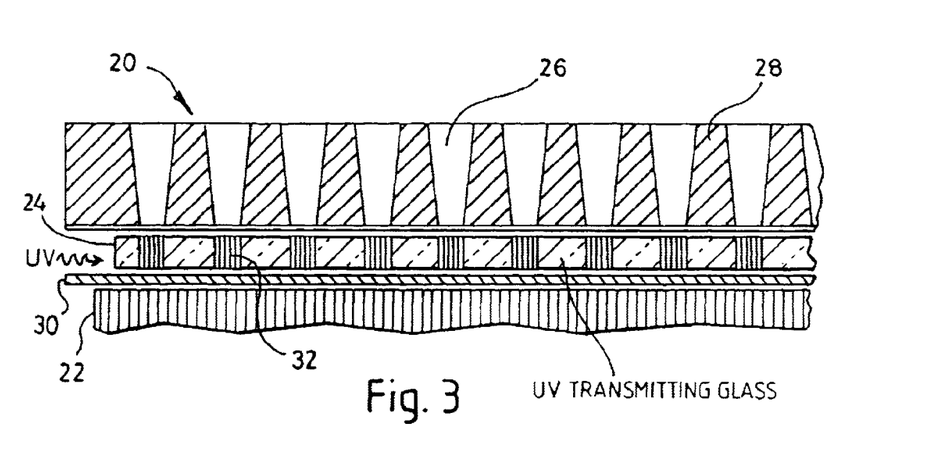
FIG. 3 is a cross-section through a preferred embodiment of the invention showing the adaptor plate sandwiched between a multi-well sample plate and a camera input window.

FIG. 3 onwards show a sample 20 coupled to a fibre optic input window 22 of an image intensifier or image intensifying CCD camera, via an adaptor plate 24. The adaptor plate can be imaged via a lens onto the input 22 albeit with reduced light gathering efficiency and a cooled CCD camera may be used in place of a standard CCD camera or image intensifier CCD camera.

The sample plate 20 comprises a rectilinear array of clear bottomed wells, one of which is denoted by reference numeral 26, separated by opaque material 28.

Underneath the plate is shown one form of adaptor plate 24 which interfaces the sample to the camera input, permitting simultaneously irradiation of a large number of sites, if not all of the sites, of the sample, with excitation light such as UV, and simultaneous collection from each of the illuminated wells, individually, of the resultant emission light.

A thin barrier filter 30 (typically less than 1 mm thick) may be inserted between the adaptor plate and the camera input, to repress UV transmission to the camera.

The adaptor plate 24 consists of a plurality of bundles 32 of optical fibres each positioned immediately under each one of the wells being interrogated. The bulk of the adaptor plate 24 is made of silica glass which transmits both UV and visible light efficiently. Holes are formed in the plate into which the bundles are secured.

The bundles 32 may be held in position by a friction fit or by an adhesive.

In each bundle the individual fibres are spaced apart and held in place by non-fluorescing material which will transmit UV, and typically silica glass is used as the binding matrix.

Although not shown, the bundle of fibres in each rod may be replaced by a single fibre provided there is a sufficient annular region around the fibre of UV transmitting matrix material through which the UV can pass into the underside of the well.

Figure 4A:
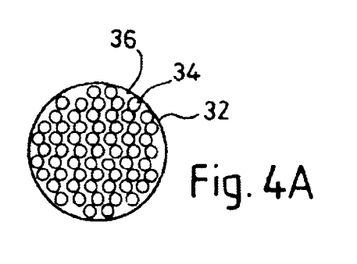
FIG. 4 is a cross-section to an enlarged scale through one of the composite transfer rods of FIG. 3.
Figure 4B:
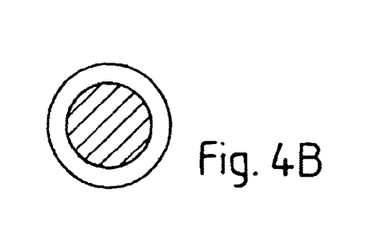

FIG. 4 shows in cross-section one of the bundles. Since the individual bundles are generally cylindrical and axially longer than their diameter, they are sometimes referred to as rods and since they can transmit both UV and ordinary light along two different paths, they are referred to as composite transfer rods.

As shown in FIG. 4, a rod comprises many optical fibres 34 arranged in a random or regular pattern, of high numerical aperture (NA), embedded in a cylindrical plug of non-fluorescing material which will transmit the excitation light. Silica glass may be used where the latter is UV. The refractive index of the silica glass ideally matches that of the material from which the bulk of the adaptor plate 24 is made, and in which the rods are embedded. To this end the adaptor plate may also be formed from silica glass.

Each fibre is sheathed or coated to prevent excitation light within the composite transfer rod from entering the fibres. The coating may be simply opaque to UV so as to block the ultra-violet. Alternatively the coating may have reflecting properties such as if a metallic material is used in which event the coating may actually serve to reflect ultra-violet. The fibres conduct any emission light arising from excitation of and subsequent fluorescence of the sample, to the imaging detector, and preserve the spacial resolution.

In general the adaptor plate 24 is coated externally with a reflecting layer to contain the excitation light therein, to aid uniform and substantially intense illumination of the sample. The excitation light can of course escape from the upper end of each rod around the fibre ends in each rod end, ie through the material denoted by the reference numeral 36 in FIG. 4.

A similar coating or blackening of the similar areas 36 at the lower end of each rod will prevent excitation light passing directly into the camera.

Figure 5:
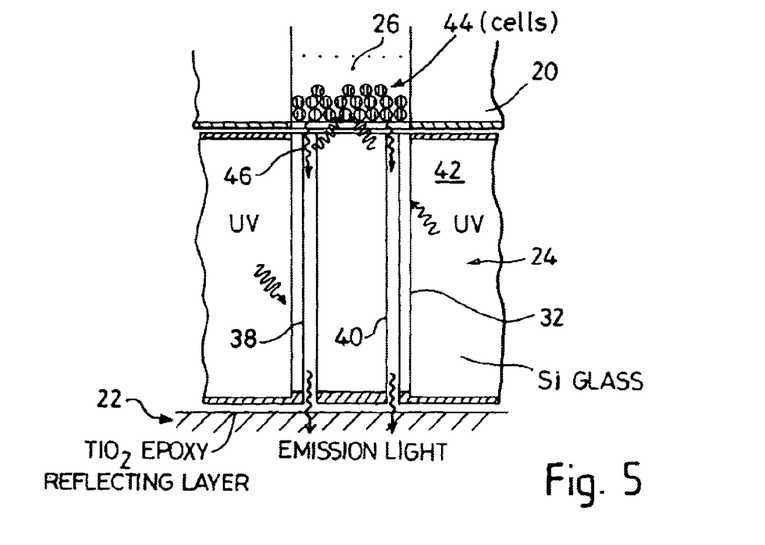
FIG. 5 is a cross-sectioned elevation through one of the composite transfer rods of FIG. 3.

FIG. 5 is a schematic side view of one of the rods.

Two of the fibres are shown at 38 and 40 within a rod 32. UV radiation 42 within the plate 24 enters the rod 32 and escapes into the well 26 in the sample plate 20 to irradiate material such as cells or molecules 44. Light emitted by them as a result of fluorescence initiated by the ultra-violet radiation, is denoted by 46, and this can pass via fibres 38, 40 to the detector input 22.

Figure 6:
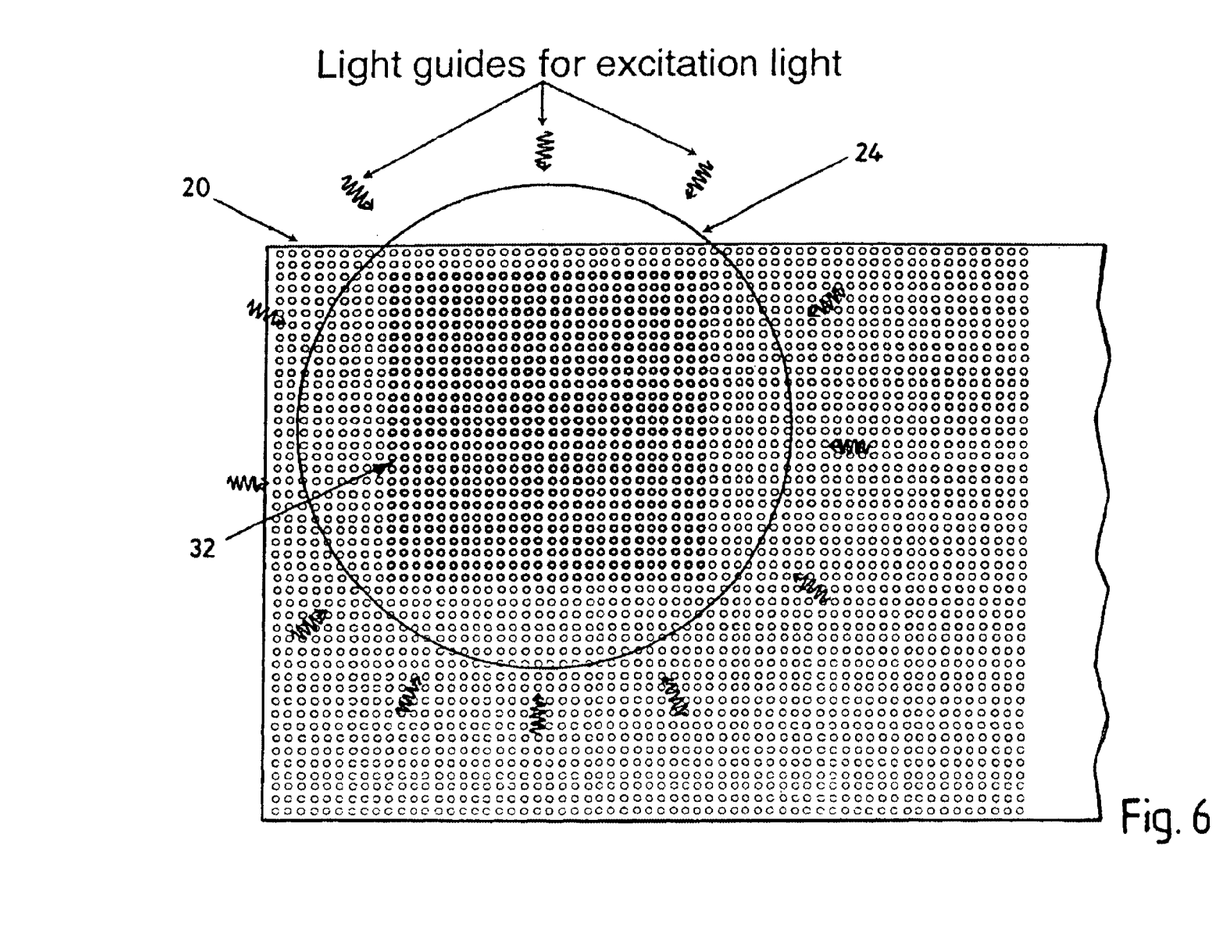
FIG. 6 illustrates how an adaptor plate can interrogate a multi-well sample plate and illustrates the registration of the composite transfer rods with the wells in the sample plate.

FIG. 6 is a schematic plan view. Here the sample being interrogated (at plate 20) is placed with its reaction sites, for examples wells 26, in registration with the transfer rods 32 in the adaptor plate 24. A portion of the sample plate 20 is interrogated at any given time and it or the adaptor plate and detector is then moved to allow another portion to be interrogated, thus effectively stepping across the sample plate. This is necessary where the sample area is greater tan the adaptor plate area and multiple images are required to "see" the whole area of the sample plate.

The excitation light is typically UV and is projected into the plate at regular intervals around its circumference by means of light guides or a suitable peripheral illumination means. This allows the use of a separate and remote UV source (not shown) which may incorporate excitation filters (not shown) including narrow band interference filters, to provide selective narrow wavelength excitation. Such filters could be arranged in a filter wheel (not shown) allowing excitation to the series of different wavelengths and if necessary at high speed. Sets of matched excitation and emission filters for given excitation sources and fluorescent applications are provided by a number of optics manufacturers, for example omega Optical Inc of Vermont, USA. Omega Filter set XF22 may be used for irradiating fluorescein. Set XF22 may be used for Fura red.

Figure 7:
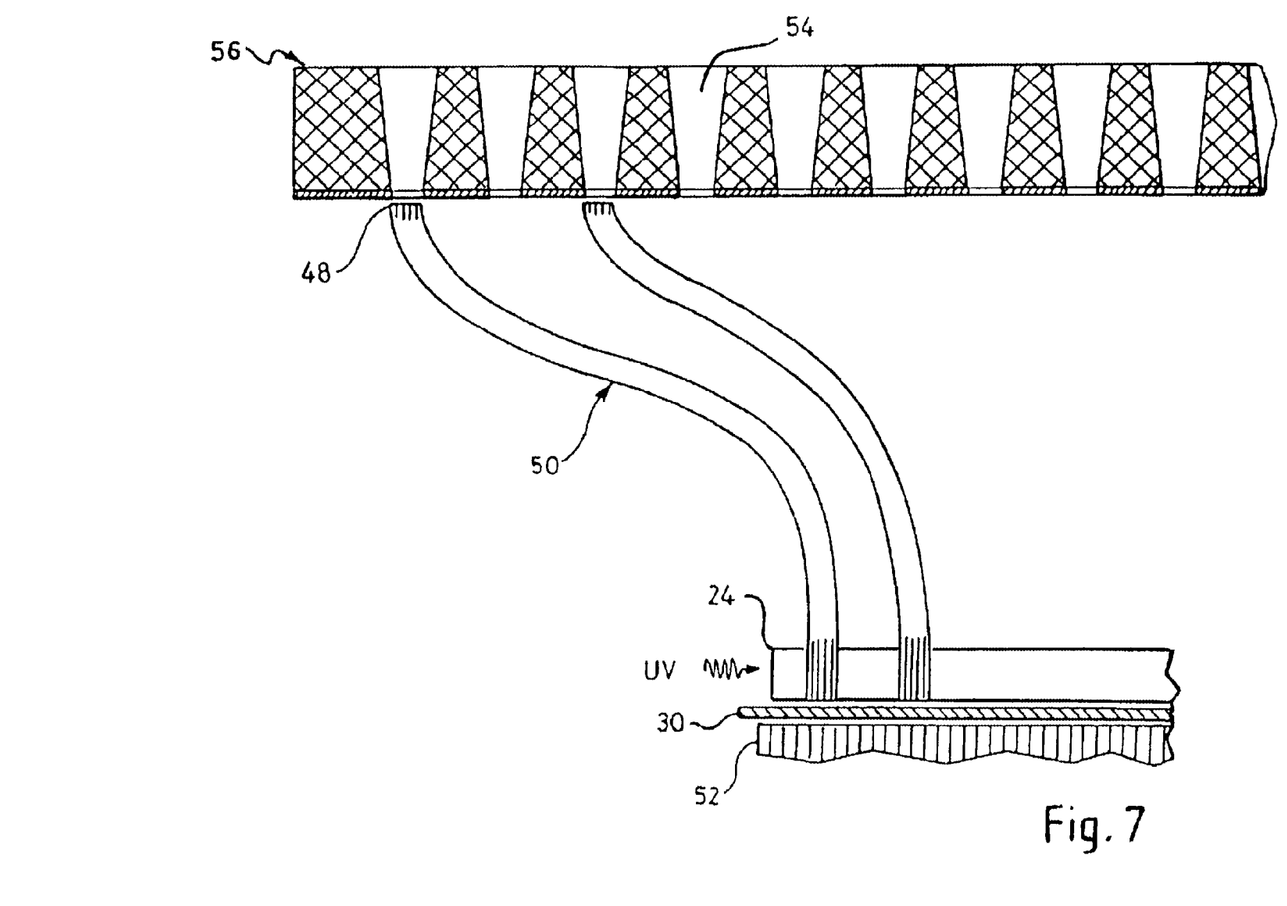
FIG. 7 shows a modification of the arrangement shown in FIG. 3 in which the composite transfer rods are extended beyond the adaptor plate.

FIG. 7 shows alternative optics in which the transfer rods 32 are extended out of the plate 24.

This is a variant of the earlier arrangement in which the adaptor plate 24 multiplexes the same geometry onto the detector via an array of composite transfer rods. In FIG. 7 the transfer rods are of the same general construction as described in relation to FIGS. 3 to 5, but are extended in length, and if so desired, with greater separation, to permit a larger area of the sample plate to be interrogated. The sample end 48 of each rod 50 interrogates a well by illuminating it with excitation light and transferring the emission light (if any) via the fibres within it to the detector or camera 52. In the example shown, the rods extend upwards to read every third well of a plate, which therefore requires two steps in the X direction and two steps in the Y direction from the position shown, for a complete read-out of the sample plate. This would be the case where an array of 96 rods interrogate a 384 well plate.

A filter 30 is shown between the plate 24 and the camera/detector input 52.

At the adaptor plate the rods can, if required, be arranged at separations and configurations different from those dictated by the placing of the wells 54 in the sample plate 56. This offers advantages at the sample end and at the camera end.

At the sample end the rods can now interrogate either adjacent or separated if so desired, for example to minimize cross-talk or to optimize sample presentation and liquid handling arrangements, where for example a liquid has to be injected into reaction sites, or for kinetics measurements where repeated measurements of reaction sites are required.

At the detector end the rods can be spaced more closely therefore better to match the camera and may be arranged as to minimize cross-talk.

Whether embedded in FIG. 3 or extended as in FIG. 7, the composite rods may taper in cross-section, ie have different input and output diameters and the fibres within the rods may also taper or be of constant diameter.

Free Format Adaptor Plate

Figure 8:
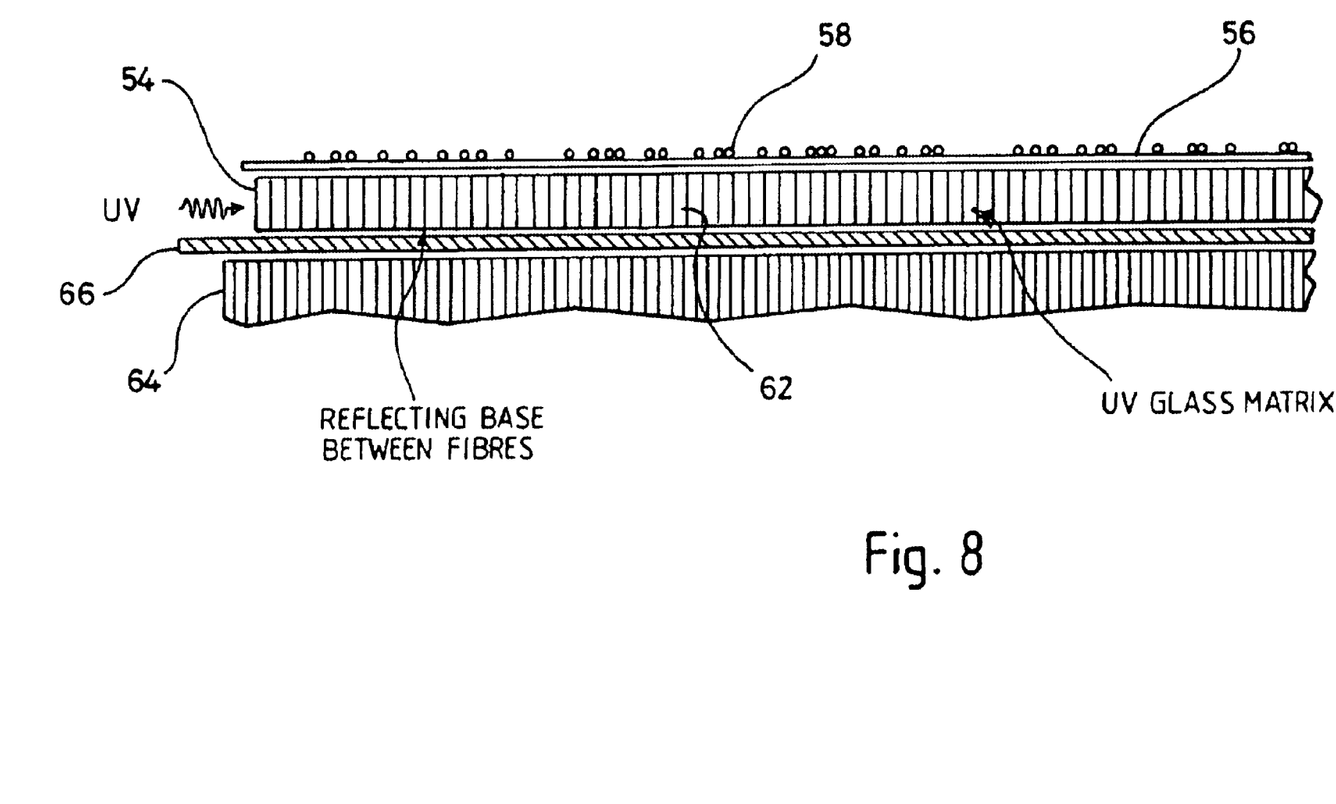
FIG. 8 is a similar view-to that of FIG. 3 of an adaptor plate constructed as another embodiment of the invention which does not require accurate registration with reaction sites or wells.
Figure 9:
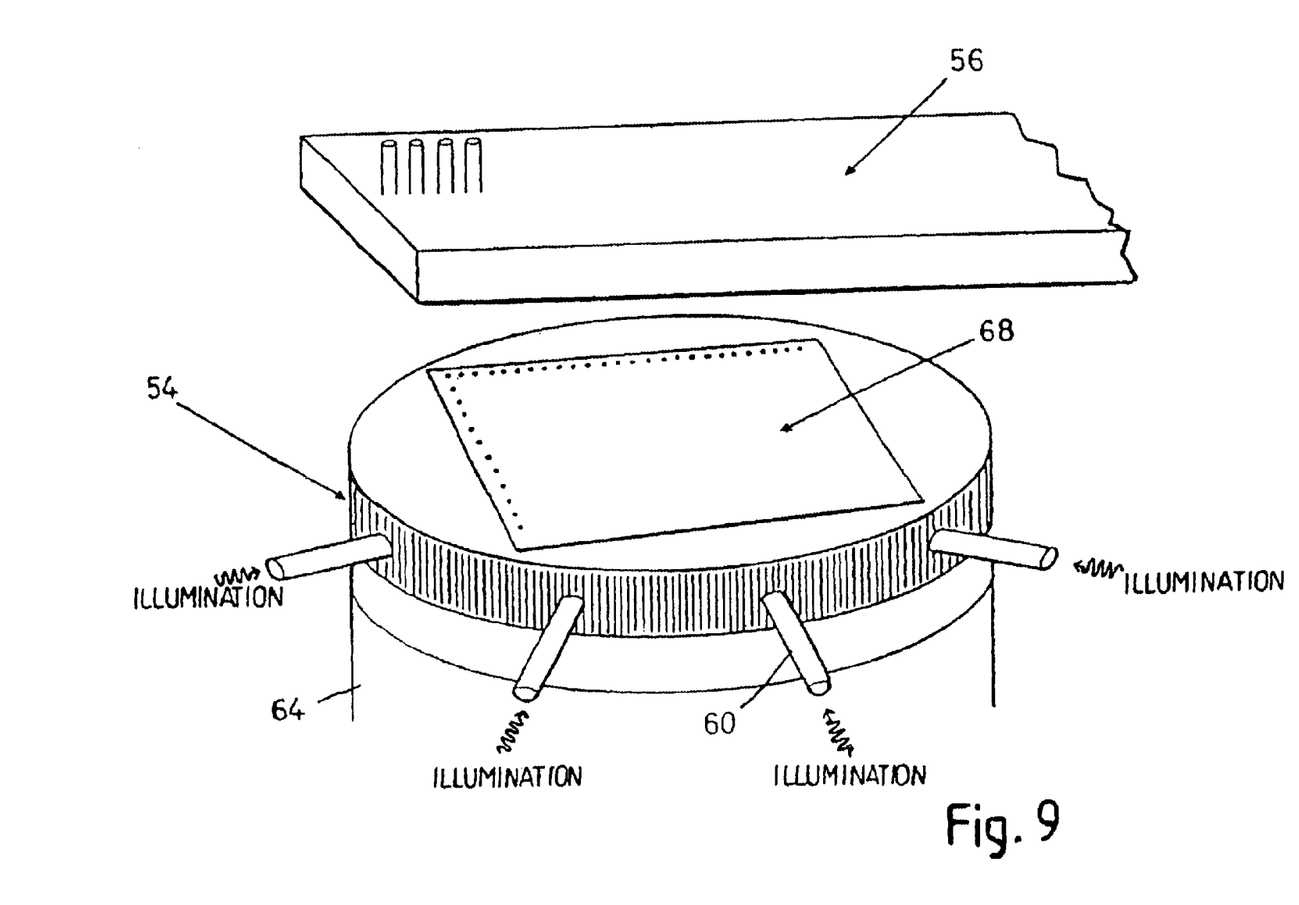
FIG. 9 shows how the adaptor plate of FIG. 8 can be modified to reduce cross-talk when used with a sample having regularly spaced apart reaction sites.

The invention can be generalized to allow imaging of a free format sample for example a random sample array such as a DNA or peptide sample on a membrane blot or gel; or cells growing in a Petri dish, or on a membrane filter. Instead of just a region under each well having a composite transfer rod with an optical fibre arrangement as described herein, the optical fibres may be distributed over the whole area of the adaptor plate. Such an adaptor plate gives total flexibility as to the position and spacing of the individual sites in the sample. Such a free format adaptor plate is shown in FIGS. 8 and 9. Here the sample comprises a membrane 56 on which there are a plurality of randomly occurring reaction sites such as 58. The membrane transmits both UV and emitted light, and UV is introduced into the plate 54 through the edges thereof via UV light guides 60 (see FIG. 9).

The plate 54 is formed from UV transmittive glass (silica glass of appropriate reflective index may be used) through which the myriads of parallel spaced apart optical fibres 62 extend. The latter are coated with UV resistant material to separate the UV from the fibres.

The image formed on the base of the plate 54 by the emitted light escaping from the fibres 62 is transferred to the input of a camera 64 through a filter 66 typically resistant to UV wavelengths.

A UV reflecting coating is applied to the base of the plate 54 but not so as to cover the ends of the fibres 62, so as to prevent UV from entering the camera/detector.

A fibre optic device is preferably employed in the window of the camera/image intensifier 64.

The fibres 62 may be arranged randomly (albeit not touching) or in a regular or irregular pattern (when viewed in plan view).

Figure 10:
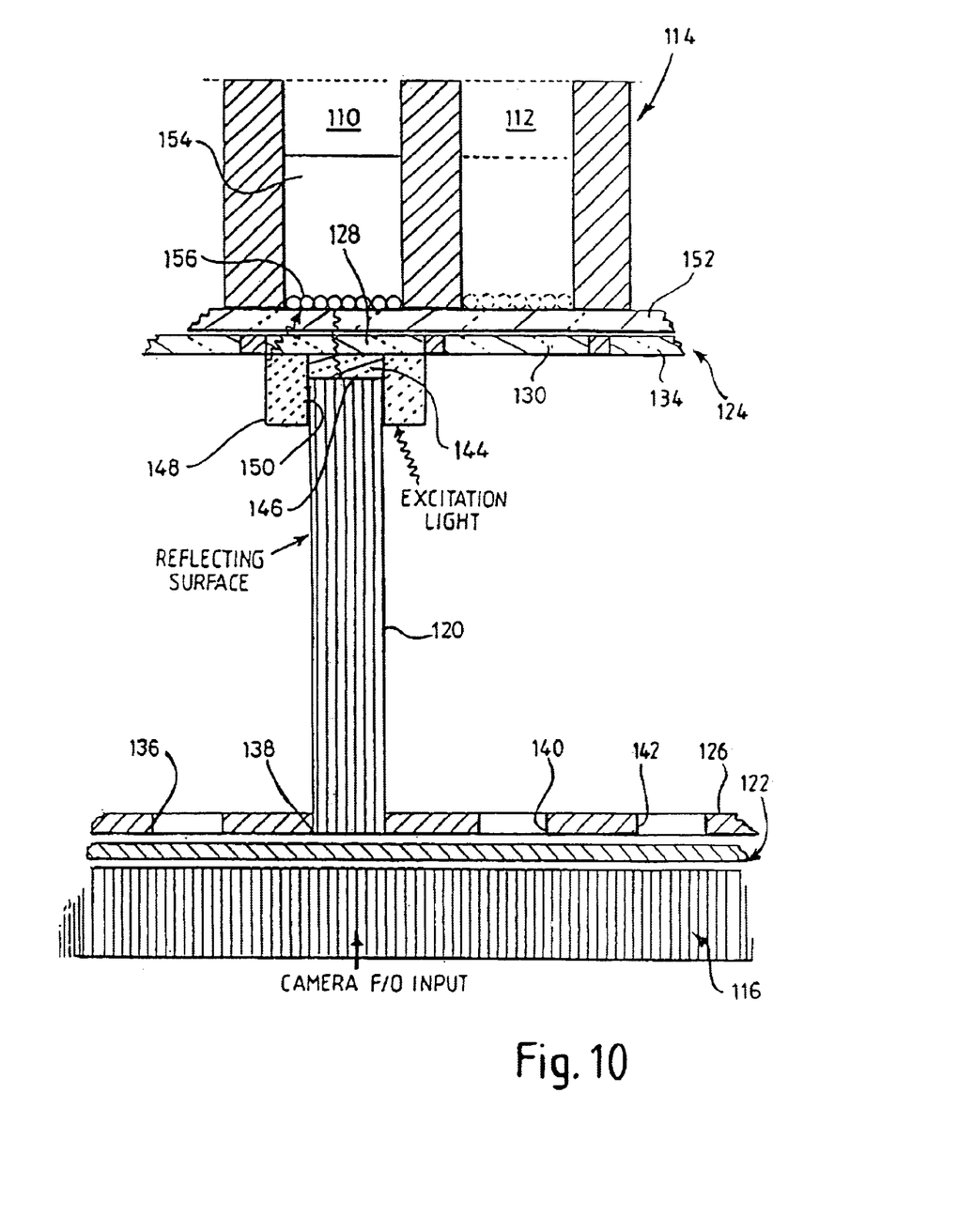
FIG. 10 is a cross-section to an enlarged scale illustrating another embodiment of the invention.
Figure 11:
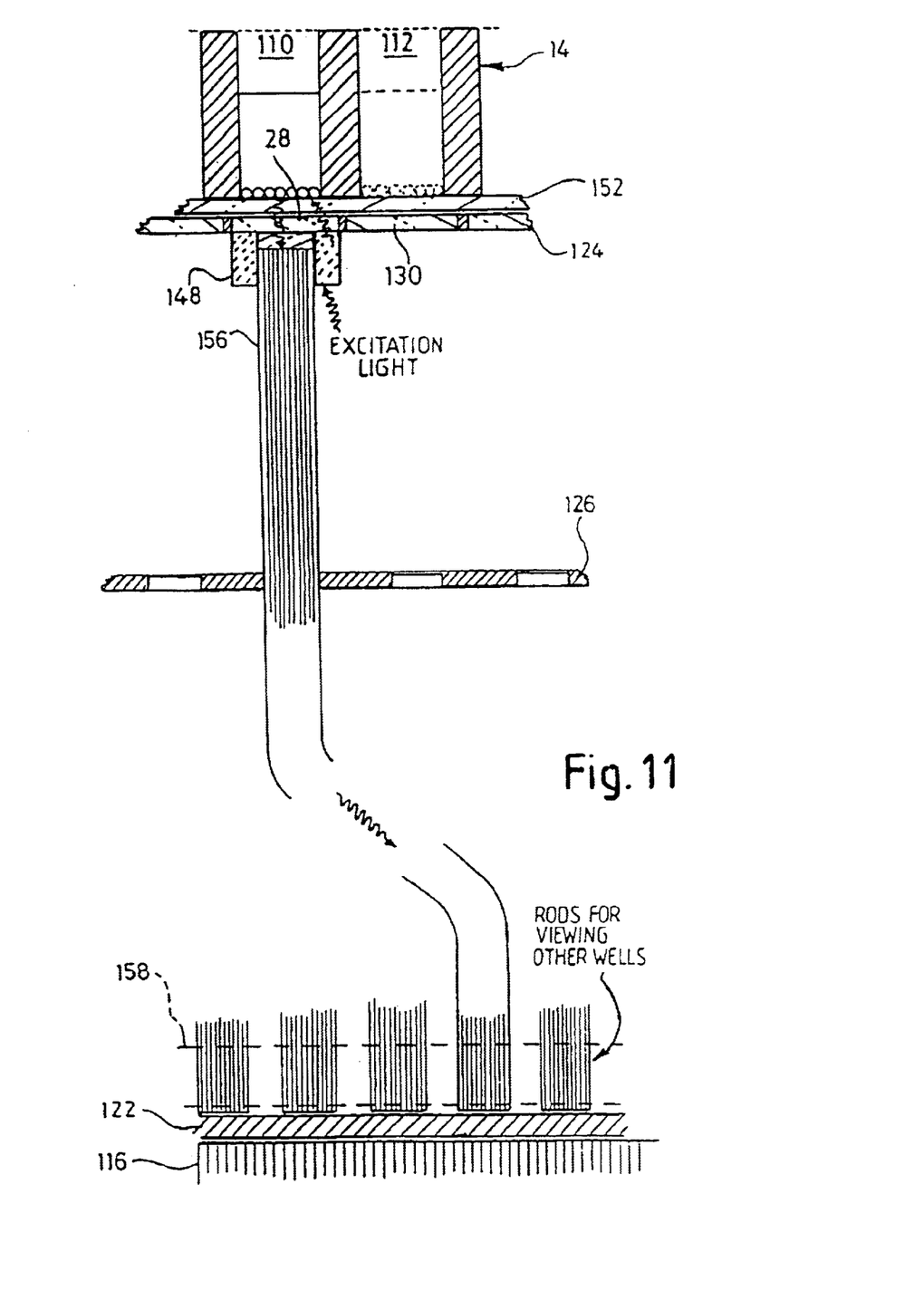
FIG. 11 is a similar schematic view of a modified version of the arrangement shown in FIG. 10.
Figure 12:
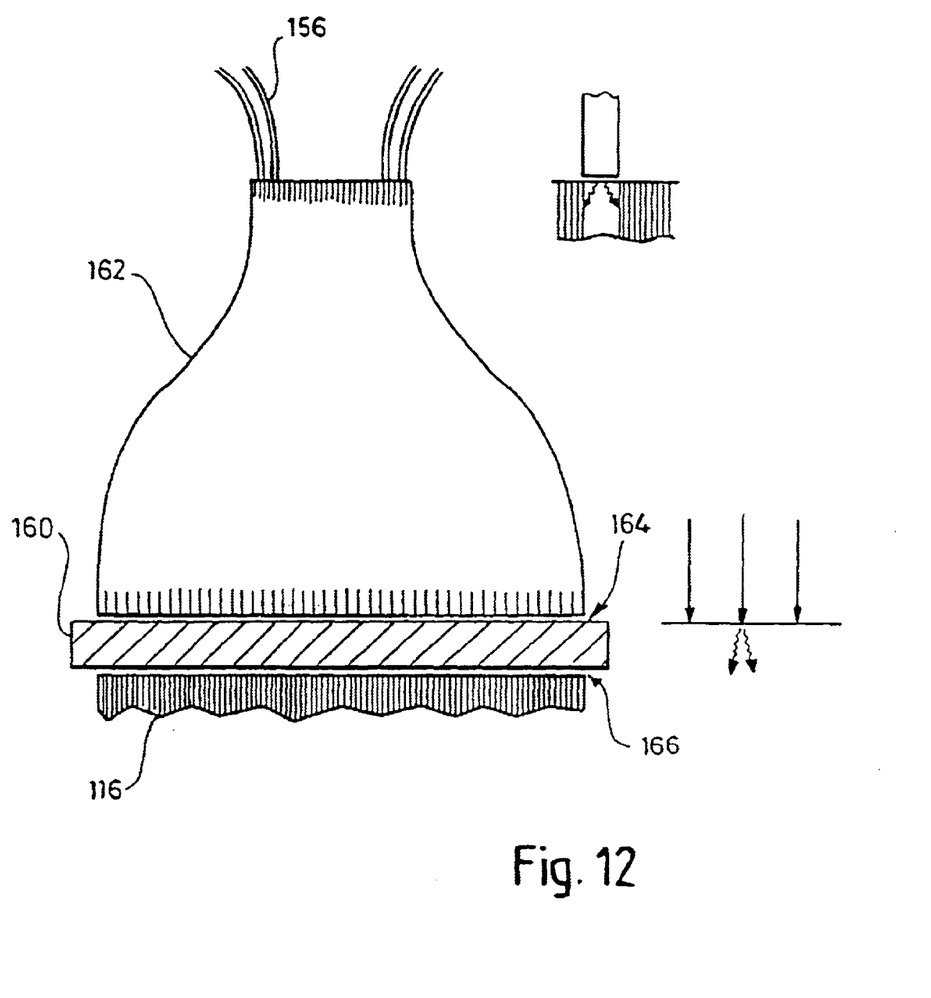
FIG. 12 is a similar schematic view of a further modified version of the arrangement shown in FIG. 10.
Figure 13:
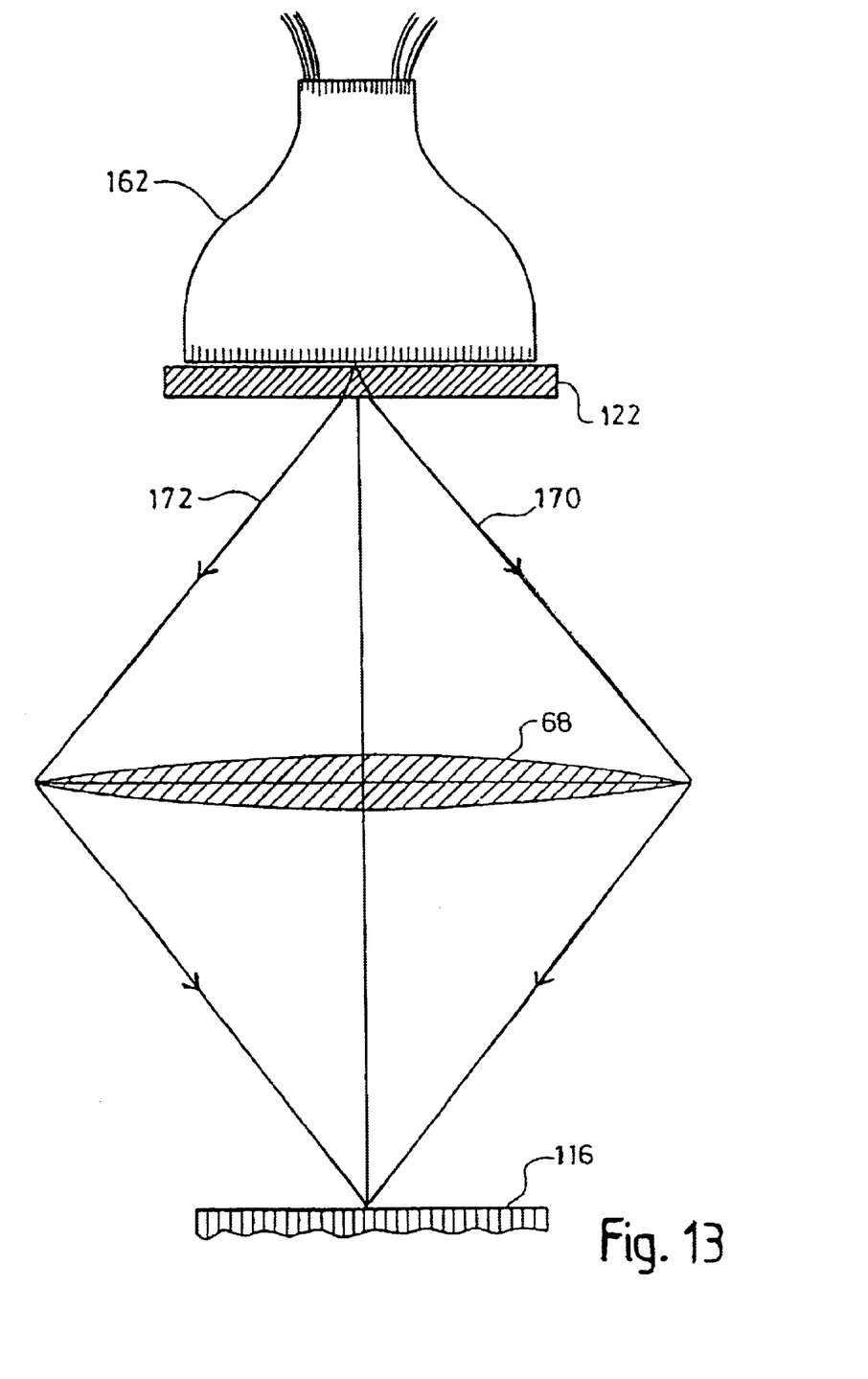
FIG. 13 is another version of the arrangement shown in FIG. 10.
Figure 14:
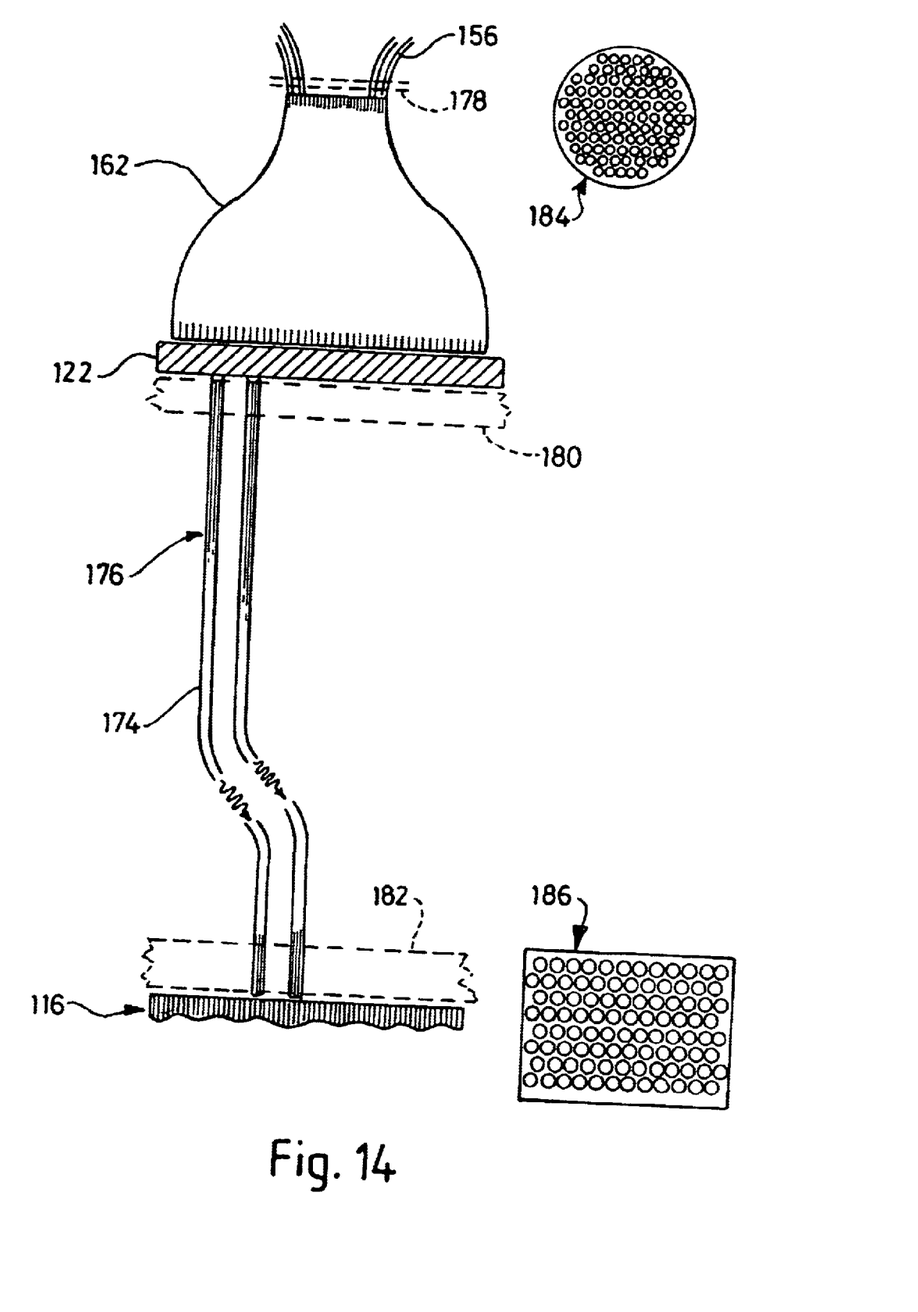
FIG. 14 is yet another schematic view of a further modified version of the arrangement shown in FIG. 10.

A further embodiment of the invention is shown in FIGS. 10 and 11.

In FIG. 10 two wells 110 and 112 forming part of a multiwell plate generally designated 114 are shown in the upper part of the drawing and a camera input window 116 is shown in the lower part of the drawing. Light emitted by a sample such as 118 in well 110 is conveyed via a fibre optic bundle 120 to the camera via a filter 122 which serves to remove unwanted wavelengths such as excitation wavelengths and spurious emissions should they occur.

The fibre optic bundles 120 are carried between two opaque plastic plates 124 and 126 which are separated and held together by a boundary wall (not shown) to form a hollow box through which the fibre optic bundles 120 extend.

The upper plate 124 is apertured as at 128 and 130, 132 and 134 and the lower plate 126 is likewise formed with openings through which the fibre optic bundles such as 120 extend. These openings are shown at 136, 138 (in the case of fibre optic bundle 120), 140 and 142.

For clarity only fibre optic bundle 120 is shown in FIG. 10, but it will be appreciated that similar bundles extend below each of the apertures 130, 132 and 134 to extend across to the apertures 140, 136 and 142 respectively in the lower plate.

In a typical arrangement, there may be as many as 96 wells in the well plate 140 and likewise 96 fibre optic bundles such as 120 which extend in alignment with each of the wells.

As shown, each of the windows such as 128, is a solid clear polystyrene material through which light can pass.

A transparent plug 144 occupies the space between the underside of the window 128 and the input face 146 of the respective fibre optic bundle 120. Typically clear polystyrene is used for the material of the plug. Alternatively the plug may be formed from a filter material so as to further assist in removing unwanted wavelength from the light passing through the fibre optic bundle 120.

An annular sleeve 148 also of polystyrene material surrounds the upper end of the fibre optic bundle 120 and the clear polystyrene plug 144. the inside cylindrical surface 150 of the sleeve 148 is formed with an opaque, possibly reflective, material so as to restrict the loss of light from any fluorescence which occurs within the sample and also restrict the entry of excitation radiation directly into the upper end 146 of the fibre optic bundle 120.

The outside surface of the fibre optic bundle or the external surface of each of the fibres making up the bundle is coated with a reflective material such as titanium dioxide. In a similar manner the inside surfaces of the two plates 124 and 126, (except where apertures or windows are formed therein) are also coated with a similar reflecting material.

The coating material is selected so as to be opaque to excitation wavelengths so as to prevent the ingress of excitation radiation into the fibre optic bundles.

In order to stimulate fluorescence, excitation radiation is directed into the hollow space between the two plates 124 and 126 and by appropriate selection of the material forming the annular sleeves, some of this radiation will pass through the sleeve material, through the clear polystyrene windows such as 128 and 130, through the material forming the base of the well plate designated by reference number 152, and into the assay contained within the well.

In known manner the assay includes materials which if subjected to excitation radiation will fluoresce at known wavelengths and it is the fluorescent emission radiation which is transmitted via the base 152 and window such as 128 into the fibre optic bundle 120 associated with the well concerned.

In the well 110, there is a liquid 154 and solid material 156, which may comprise phosphor coated particles having part of the assay on their surface. In accordance with known techniques the other labelled phase of the assay exits in or is introduced into the liquid, and the binding of the two parts of the assay is indicated by the degree of fluorescence from the sample.

Unlike the fibre optic bundle described in relation to FIG. 1, the optical fibres making up the bundle 120 are grouped together and are touching so as to form a rod and there are no spaces between the fibres through which excitation radiation can enter and along which such radiation can pass into the well 110. Instead all excitation radiation entering the well must pass through the annular sleeve 148.

The latter may be formed from polystyrene which may be translucent, as opposed to transparent, so as to diffuse any radiation passing therethrough to produce more even illumination of the well.

As hitherto described, the fibre optic bundles making up the transfer rods can be grouped differently at the output end of the plate from the arrangement at the input face of the plate, in which the number and spacing and size is dictated by the arrangement of the wells in the sample plate. This enables any desired arrangement or pattern of fibre optic bundle ends to be presented to the filter.

In FIG. 11 the same reference symbols have been used as in FIG. 10 to denote similar items but the fibre optic bundle 120 is now designated by reference number 156, since instead of terminating at the lower plate 126, the fibre optic bundle carries on through the plate 126, and is re-arranged in position relative to the other fibre optic bundles extending through the plate 126, so as to be positioned as required adjacent the input face of the filter 122. In order to maintain the registration of the output ends of the fibre optic bundles such as 156, an exit plate 158 (shown in dotted outline), is provided with appropriate apertures within which the lower ends of the fibre optic bundles 156 are embedded.

Where the field of view of the camera has an aspect ratio of say 4:3, the array of fibre optic bundles in the plate 158 is arranged so as to approximate to that ratio. Where there are 96 wells and 96 fibre optic bundles, the latter may be arranged in 12 rows, each containing 8 bundles. In this way the image presented to the camera can be optimized.

If the area available at the camera input is insufficient to accommodate the total area of the fibre optic bundles presented thereto, the optical fibres making up each bundle may be tapered in cross-section from the input to output, so that the area of the bundle presented to the filter is smaller than the area of the fibre optic bundle presented to the well plate. This allows for a greater packing density of fibre optic bundles at the camera input. However it may also result in light loss and other undesirable optical effects and alternative techniques are preferred.

General Construction and Design Points

The adaptor plate is of silica glass and has a diameter to match camera input, with composite transfer rods glued into a pattern of holes matching the positions and spacing of the wells. Excitation light enters the plate through light guides placed around the circumference of the plate, and excitation light passes from the plate into the rods and thence into the wells.

Composite transfer rods should have the same diameter as the wells, and typically will be 1 mm in diameter. Each rod comprises optical fibres each of diameter 0.1 mm having a numerical aperture (NA) of 1.0 for emission light, but being non-UV transmitting. Each fibre has a UV blocking/reflecting coating or sheath. The fibres are set in and extended through a block of UV transmitting, non-fluorescing glass, with approximately the same refractive index as the material from which the remainder of the adaptor plate is formed. The surface of each rod under each well is polished and in contact with (or very slightly spaced from) the flat transparent well bottom. Excitation light can enter the bottom of the well at many different angles. The emission light is accepted within the NA of the conducting fibres and is conveyed to the bottom of the rod along the fibres. The material from which the fibres are made blocks the leakage of UV through the rod.

The remaining surfaces of the adaptor plate are coated for example with titanium dioxide/epoxy to form a reflecting layer. Silica glass at the bottom of each rod is etched back to allow coating or selective blackening.

Where each rod is nominally of 1 mm diameter, it can container perhaps 80 fibres each of a diameter 0.1 mm so that approximately 80% of the area of the rod is available for collection of emission light, and 20% of the cross-section of the rod is available for the transmission of excitation light.

The adaptor plate can be stood off from the camera input to allow the insertion of a thin emission filter without serious cross-talk between wells.

The efficiency of light reflection up to the input faceplate of a camera is given by the expression on the next line:

$$0.8 * \left(\frac{1}{1.5}\right)^2 = 36\%$$

The first factor is the fraction of fibres in the rod and the second is the effect of the numerical aperture (NA) of a fibre viewing a liquid in a well.

The excitation source of the ultra-violet can utilize parallel optics and hence incorporate interference filters in a free standing source. Light transferred to the circumference of the adaptor plate with light guides (such as liquid light guides having a numerical aperture of 0.47) will give 60% transmittance at wavelengths of the order of 350 nm.

What is claimed is:

1. Apparatus comprising:
   (1) a fibre optic coupling device for use in combination with a sample having a plurality of regularly spaced apart sites thereon, each site having the same diameter as each of the other sites, a detector and a source of excitation radiation, wherein the device has primary light paths which convey fluorescence light from the sites to the detector and secondary light paths by which excitation radiation is separately conveyed to the sample to irradiate the sites to cause said fluorescence, and wherein each of the paths is formed from optical fibres, and in said device:
   (i) fibres from each of the two paths are merged into a plurality of composite bundles at one end in the same pattern and with the same intersticial spacing as the sites in the sample to transmit excitation light into and receive fluorescence light from a corresponding plurality of sites on the sample;
   (ii) the bundled fibres occupy discrete areas, each of which registers with one of the sites in the sample and is commensurate with but a little smaller than the cross sectional area of the sample site from which radiation may be emitted into the bundle;
   (iii) all of the fibres are of the same cross-sectional size; and
   (iv) the other ends of the fibres from each bundle which form the primary path are bundled separately from those constituting each of the other primary paths; and wherein
   (2) the detector comprises a CCD camera having a fibre optic faceplate, the separately bundled primary path fibres terminating at the faceplate of the COD camera and the primary path fibre bundles being arranged over the faceplate so as to approximate to the aspect ratio of the camera field of view, and thereby optimise the imaging of the sample sites at the camera;
   (3) the other ends of the fibres from each bundle which form one of the secondary paths being all bundled together to receive radiation from the source of excitation radiation, and simultaneously convey that radiation respectively to each of the sample sites which register with a composite fibre bundle; and
   (4) means for preventing excitation radiation from reaching the COD camera faceplate.

2. Apparatus according to claim 1 wherein the preventing means comprises absorbing means to restrict the exit of excitation radiation except as required to irradiate the sample sites.

3. Apparatus according to claim 1, in which the primary light path fibres are formed from a material which readily transmits light emitted from the sample but only poorly transmits excitation radiation wavelengths.

4. Apparatus according to claim 1, wherein the number of fibre bundles is a fraction of the number of sites in the sample and all of the latter can be inspected, by moving the sample relative to the coupling device (or vise versa) in a sequence of steps until all the sites have been brought into registration with the bundles of fibres once during the said sequence of steps.

5. Apparatus according to claim 1, wherein the device has an output window viewed by the camera wherein each optical fibre bundle forming the primary light path therein receives emission radiation from a single sample site, and transfers the emission radiation from that site to a discrete region of the output window.

* * * * *